US010620225B2

(12) United States Patent
Benchikh et al.

(10) Patent No.: US 10,620,225 B2
(45) Date of Patent: Apr. 14, 2020

(54) DETECTION OF POLYMYXINS (71) Applicant: Randox Laboratories Limited, Crumlin (GB)

(72) Inventors: Elouard Benchikh, Crumlin (GB); Ivan McConnell, Crumlin (GB); Philip Lowry, Crumlin (GB); Peter Fitzgerald, Crumlin (GB)

(73) Assignee: Randox Laboratories Limited, Crumlin (GB)

( * ) Notice: Subject to any disclaimer, the term of this patent is extended or adjusted under 35 U.S.C. 154(b) by 329 days.

(21) Appl. No.: 14/873,109

(22) Filed: Oct. 1, 2015

(65) Prior Publication Data
US 2016/0097784 A1 Apr. 7, 2016

(30) Foreign Application Priority Data

Oct. 1, 2014 (GB) .................................. 1417384.3

(51) Int. Cl.
| | |
|---|---|
| *G01N 33/94* | (2006.01) |
| *C07K 7/64* | (2006.01) |
| *C12N 9/96* | (2006.01) |
| *G01N 33/535* | (2006.01) |
| *C07K 16/44* | (2006.01) |
| *C07K 17/02* | (2006.01) |
| *G01N 33/532* | (2006.01) |
| *C07K 16/12* | (2006.01) |
| *C12N 9/08* | (2006.01) |
| *C07K 7/62* | (2006.01) |
| *A61K 38/00* | (2006.01) |

(52) U.S. Cl.
CPC ........... *G01N 33/9446* (2013.01); *C07K 7/62* (2013.01); *C07K 7/64* (2013.01); *C07K 16/1267* (2013.01); *C07K 16/44* (2013.01); *C07K 17/02* (2013.01); *C12N 9/0065* (2013.01); *C12N 9/96* (2013.01); *G01N 33/532* (2013.01); *G01N 33/535* (2013.01); *A61K 38/00* (2013.01); *C12Y 111/01007* (2013.01); *G01N 2410/00* (2013.01)

(58) Field of Classification Search
None
See application file for complete search history.

(56) References Cited

U.S. PATENT DOCUMENTS

2003/0157565 A1* 8/2003 Lamont ................ C07D 489/02
435/7.1

FOREIGN PATENT DOCUMENTS

| CN | 101358966 A | 2/2009 |
|---|---|---|
| JP | 50089390 A | 7/1995 |

OTHER PUBLICATIONS

Englebienne, "Immune and Receptor Assays in Theory and Practice," CRC Press, 2000, p. 308.*
Creative Diagnostics, Specification Sheet "Colistin & polymyxin ELISA Kit," Rev 110704HH, posted on Internet (http://www.funakoshi.co.jp/data/datasheet/CDG/DEIA042.pdf) on Jul. 12, 2011.*
Falagas et al., "Colistin: The Revival of Polymyxins for the Management of Multidrug-Resistant Gram-Negative Bacterial Infections," Clin. Infect. Diseases, 2005, vol. 40, issue 9, pp. 1333-1341.*
The European Medicines Agency Report, 2013, pp. 1-25.*
Kitagawa et al., "Sensitive enzyme immunoassay of colistin and its application to detect residual colistin in rainbow trout tissue," J. Assoc. Off. Anal. Chem., 1985, vol. 68, No. 4, pp. 661-664.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
AAT Bioquest® "SMCC and SMCC Plus™ Protein Crosslinkers," Product Technical Information Sheet, 2012.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
A printout retrieved from http://affiliateswitchblade.com/blog/how-to-find-out-when-a-pdf-document-was-published/ on Aug. 26, 2019.*
Creative Diagnostics, Specification Sheet "Colistin & polymyxin ELISA Kit," Rev 110704HH, retrieved from http://img.creative-diagnostics.com/pdf/DEIA042%20Colistin%20&%20polymyxin%20ELISA%20Kit.pdf on Aug. 26, 2019.*
Search Report from parent United Kingdom Application No. 1417384. 3, 2 pages (dated Jun. 18, 2015).
Saita et al., "A Highly Sensitive Elisa for the Quantification of Polymyxin B Sulfate in Human Serum," Biol. Pharm. Bull. 22(12):1257-1261 (1999).
Kurihara et al., "Studies on the Compounds Related to Colistin X. Synthesis and Antibacterial Activity of Colistin Derivatives," *Yakugaku Zasshi* 94:1414-1418 (1975)(w/English Abstract).
Wild, David, ed., "The Immunoassay Handbook", Third Edition, Oxford, UK: Elsevier (2005) p. 461.

* cited by examiner

*Primary Examiner* — Galina M. Yakovleva
(74) *Attorney, Agent, or Firm* — Womble Bond Dickinson (US) LLP (57) ABSTRACT

The present invention relates to antibodies for use in detecting polymyxins and tracers; and to a single-capture immunodetection method and kits, each utilising the antibodies of the invention, and disclosed tracers.

10 Claims, 5 Drawing Sheets

Colistin A: R=5-methylheptyl
Colistin B: R=5-methylhexyl

Polymyxin B$_1$: R=5-methylheptyl
Polymyxin B$_2$: R=5-methylhexyl

Phe= phenylalanine
Leu= leucine
Thr= threonine
Dab= diaminobutyric acid

FIG. 5

DETECTION OF POLYMYXINS

PRIORITY CLAIM

This claims the benefit of United Kingdom Application No 1417384.3, filed Oct. 1, 2014, which is incorporated herein by reference.

FIELD OF THE INVENTION

The present invention relates to antibodies for use in detecting polymyxins and tracers; and to a single-capture immunodetection method and kits, each utilising the antibodies of the invention, and disclosed tracers.

BACKGROUND TO THE INVENTION

Polymyxins are a family of antibacterial agents comprising a cyclic peptide structure composed of diaminobutryic acid moieties and various essential amino acids together with a hydrophobic tail. Polymyxins are produced in gram-positive bacteria and act primarily on gram-negative bacteria by disruption of the outer membrane of the gram-negative bacterium. Of the recognized polymyxins, Polymyxin B and Polymyxin E (colistin) are each used therapeutically, each having been shown to be active against inter alia *Pseudomonas aeruginosa*, Enterobacteriaceae (such as *E. coli, Klebsiella pneumoniae*) and *Acinetobacter* spp. The toxicity of polymyxins has limited their therapeutic use to topical administration and as a last line of defense against life-threatening infections caused by bacteria resistant to standard antibiotics. Colistin and Polymyxin B have been used as veterinary medicines for several decades as treatment for gram-negative gastrointestinal infections in densely populated livestock. As a result, there are increasing reports of bacterial resistance.

The rise in multi-drug resistant bacteria, thought to be primarily as a result of antibiotic over-prescribing in humans and especially over-use in domestic animals (including prophylactic prescribing), highlights the need to moderate the use of last resort treatments such as the polymyxins. A recent report by the European Medicines Agency (2013) recommends rational antimicrobial therapy including cessation of both use in control and treatment of *Salmonella* spp. in poultry and pigs, and in production enhancement e.g. increase of feed efficiency or growth promotion. Furthermore, the European Agency for the Evaluation of Medicinal Products (2002) and the Codex *Alimentarius* Commission have set the maximum residue limit (MRL) for Colistin in various animal tissues at 50-300 µg/kg. The implementation of such requirements and recommendations requires Colistin and Polymyxin B testing methods.

An ELISA for the quantification of Polymyxin B sulphate in human serum is known. The immunogen used to derive the antibodies used in the immunoassay was Polymixyin B bonded to the primary amino groups of the diaminobutyric moieties of Polymyxin B via the crosslinking group N-(gamma-Maleimidobutyryloxy)succinimide (GMBS). The resultant antibodies were cross-reactive to Polymyxin B but not Colistin. Colistin specific antibodies are also known. There is also a commercially available ELISA which detects both Colistin and Polymyxin B using an indirect competitive immunoassay format with Colistin and Polymyxin B spotted on a microtitre plate. The antigens Colistin and Polymyxin B are both spotted on the microtitre plate, which implies that the assay incorporates a mixture of antibodies, one of which binds to Colistin and one of which binds to Polymyxin B.

Thus, previous immunogens used to raise antibodies to polymyxins make use of the parent Polymyxin B structure and appear to use a scattergun approach when synthesizing the hapten in which all of the five primary amine groups are open to derivatisation. This non-targeted approach, in which all of the primary amino groups are liable to bonding, may be the reason that the subsequently raised antibody does not exhibit appreciable binding to both Polymyxin B and Colistin as it is possible that the epitopes of the target peptide are masked by the conjugated carrier proteins.

Figure 5:
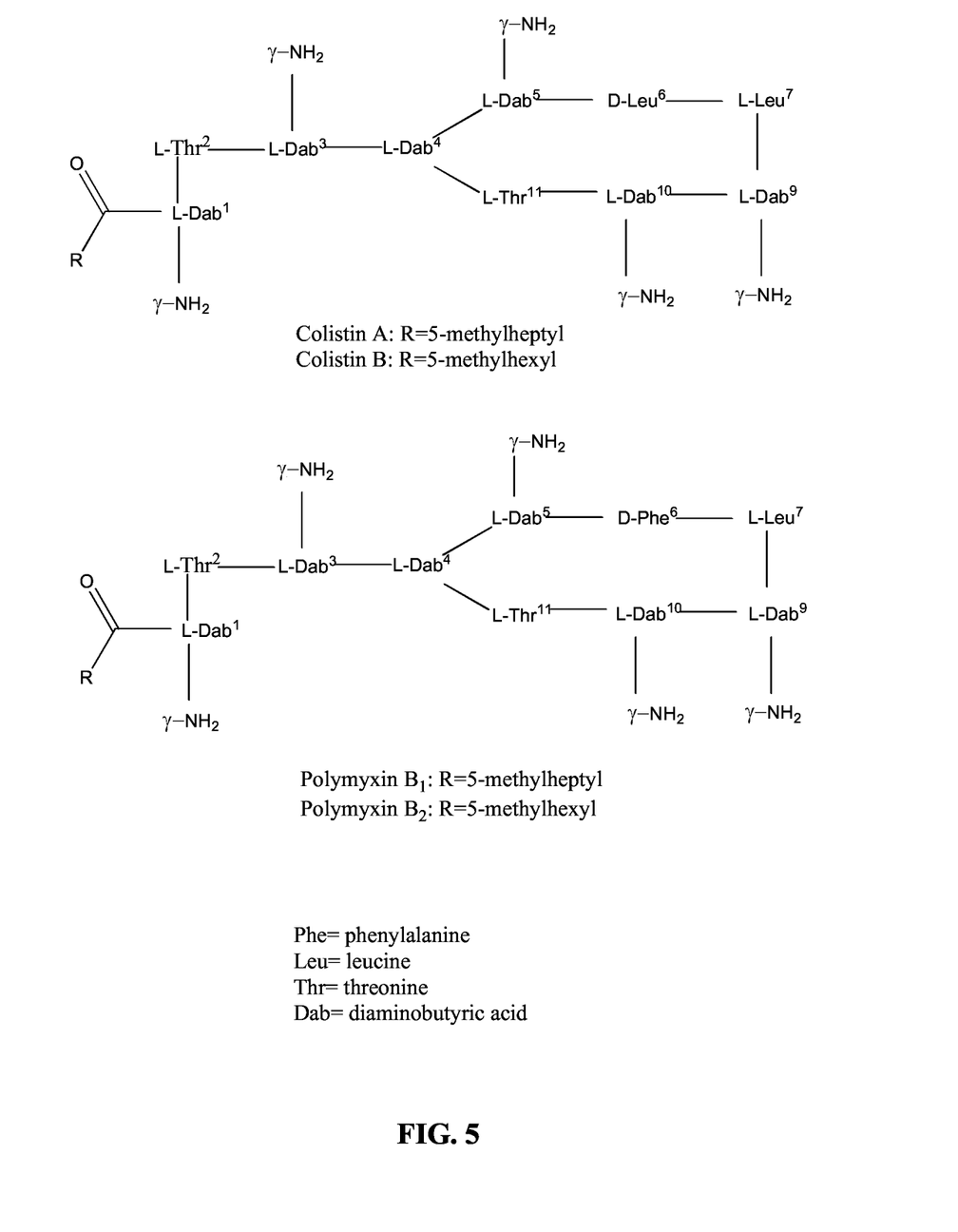
FIG. 5 illustrates Colistin A and Colistin B, Polymyxin B1, and Polymyxin B2.

Polymyxin B and Colistin commercial formulations each exist as mixtures of chemically related compounds, with the main polymyxin variants being Polymyxin B1 and Polymyxin B2 and the main colistin variants being Colistin A and Colistin B; and, in each of which the fatty acid terminal group is varied—being either a 5-methylheptyl or 5-methylhexyl chain (see FIG. 5).

SUMMARY OF THE INVENTION

According to a first aspect of the present invention, there is provided a hapten, immongen, or tracer having the general formula of Structure I:

Structure I wherein;

for the hapten, R is selected from the group consisting of benzyl and isobutyl; X1, X2, and X3 are each independently selected from the group consisting of a hydrogen atom (H) and SH—Z—, in which Z is a substituted or unsubstituted, straight or branched alkyl group, optionally a substituted or unsubstituted, straight or branched alkyl group of 1-10 carbon atoms;

for the immunogen, R is selected from the group consisting of benzyl and isobutyl; X1, X2, and X3 are each independently selected from the group consisting of a hydrogen atom (H) and [accm-spacer-], wherein accm is an antigenicity conferring carrier material; and for the tracer, R is selected from the group consisting of benzyl and isobutyl; X1, X2, and X3 are each independently selected from the group consisting of a hydrogen atom (H) and [HRP-spacer-], wherein HRP is horseradish peroxidase.

Optionally at least one of X1, X2, and X3 is a hydrogen atom (H). Further optionally, at least two of X1, X2, and X3 is a hydrogen atom (H). Still further optionally, each of X1 and X3 is a hydrogen atom (H).

Optionally, Z is a substituted or unsubstituted alkyl group. Further optionally, Z is a substituted or unsubstituted, straight or branched chain alkyl group. Still further optionally, Z is a substituted or unsubstituted, straight or branched chain alkyl group of 1-10 carbon atoms.

Optionally, Z is a substituted, straight or branched chain alkyl group of 1-10 carbon atoms.

Optionally, Z is a substituted, straight chain alkyl group of 1-10 carbon atoms.

Optionally, Z is a substituted, straight chain alkyl group of 3 carbon atoms.

Optionally, Z is —CH$_2$—CH(NH$_2$)—C(O)—.

Optionally, the spacer is selected from any molecule having a chemical group capable of forming a bond between X1, X2, or X3 and the respective nitrogen atom (N) of Structure I. Further optionally, the spacer is selected from any molecule having chemical group capable of forming a bond between the accm or HRP at any one of X1, X2, and X3 and the respective nitrogen atom (N) of Structure I.

Optionally, the spacer is selected from one or more of the group consisting of a substituted or unsubstituted alkyl group, a substituted or unsubstituted alkenyl group, a substituted or unsubstituted cycloalkyl group, a substituted or unsubstituted heterocyclyl group, a substituted or unsubstituted aryl group, and a substituted or unsubstituted heteroaryl group.

Optionally, the spacer is a substituted or unsubstituted alkyl group. Further optionally, the spacer is a substituted or unsubstituted, straight or branched chain alkyl group. Still further optionally, the spacer is a substituted or unsubstituted, straight or branched chain alkyl group of 1-10 carbon atoms.

Optionally, the spacer is a substituted or unsubstituted, straight or branched chain alkyl group of 1-10 carbon atoms and having terminal heteroatoms, functional groups, or transformed functional groups.

Optionally, the spacer is a substituted or unsubstituted, straight or branched chain alkyl group of 1-10 carbon atoms and having a terminal thiol group.

Optionally, the spacer is —S—Y—, wherein S is attached to the accm or HRP and Y is a substituted or unsubstituted, straight or branched chain alkyl group of 1-10 carbon atoms.

Optionally, the spacer is —S—Y—, wherein S is attached to the accm or HRP and Y is a substituted, straight or branched chain alkyl group of 1-10 carbon atoms.

Optionally, the spacer is —S—Y—, wherein S is attached to the accm or HRP and Y is a substituted, straight chain alkyl group of 1-10 carbon atoms.

Optionally, the spacer is —S—Y—, wherein S is attached to the accm or HRP and Y is a substituted, straight chain alkyl group of 3 carbon atoms.

Optionally, the spacer is —S—CH$_2$—CH(NH$_2$)—C(O)—.

Optionally, the accm is selected from a molecule capable of promoting immunogenicity.

Optionally, the accm is selected from a molecule comprising poly(amino acid) segments. Further optionally, the accm is selected from the groups consisting of polypeptides, proteins, and protein fragments.

Optionally, the accm is selected from the group consisting of keyhole limpet haemocyanin (KLH), bovine thyroglobulin (BTG), bovine serum albumin (BSA), egg ovalbumin, bovine gamma globulin, and cationised BSA.

Optionally, the accm is selected from the group consisting of carbohydrates, yeasts, and polysaccharides.

Optionally, the accm further comprises a maleimide group.

Optionally, the HRP further comprises a maleimide group.

Optionally, the hapten has the general formula of Structure I; wherein R is selected from benzyl and isobutyl; X1, X2, and X3 are each independently selected from a hydrogen atom (H) and SH—Z—, in which Z is a substituted or unsubstituted, straight or branched alkyl group, optionally a substituted or unsubstituted, straight or branched alkyl group of 1-10 carbon atoms.

Optionally at least one of X1, X2, and X3 is a hydrogen atom (H). Further optionally, at least two of X1, X2, and X3 is a hydrogen atom (H). Still further optionally, each of X1 and X3 is a hydrogen atom (H).

Optionally, the hapten has the general formula of Structure I; wherein R is selected from benzyl and isobutyl; each of X1 and X3 is a hydrogen atom (H); and X2 is SH—Z—, in which Z is a substituted or unsubstituted, straight or branched alkyl group, optionally a substituted or unsubstituted, straight or branched alkyl group of 1-10 carbon atoms.

Optionally, the hapten has the general formula of Structure I; wherein R is selected from benzyl and isobutyl; each of X1 and X3 is a hydrogen atom (H); and X2 is SH—Z—, in which Z is —CH$_2$—CH(NH$_2$)—C(O)—.

Optionally, the hapten has the general formula of Structure I; wherein R is selected from benzyl and isobutyl; each of X1 and X3 is a hydrogen atom (H); and X2 is SH—CH$_2$—CH(NH$_2$)—C(O)—.

Optionally, the immunogen has the general formula of Structure I; wherein R is selected from benzyl and isobutyl; X1, X2, and X3 are each independently selected from a hydrogen atom (H) and [accm-spacer-], wherein accm is an antigenicity conferring carrier material.

Optionally, the immunogen has the general formula of Structure I; wherein R is selected from benzyl and isobutyl; each of X1 and X3 is a hydrogen atom (H); and X2 is [accm-spacer-], wherein accm is an antigenicity conferring carrier material.

Optionally, the immunogen has the general formula of Structure I; wherein R is selected from benzyl and isobutyl; each of X1 and X3 is a hydrogen atom (H); and X2 is [accm-spacer-], wherein accm is an antigenicity conferring carrier material, and spacer is a substituted or unsubstituted, straight or branched chain alkyl group of 1-10 carbon atoms and having terminal heteroatoms, functional groups, or transformed functional groups.

Optionally, the immunogen has the general formula of Structure I; wherein R is selected from benzyl and isobutyl; each of X1 and X3 is a hydrogen atom (H); and X2 is [accm-spacer-], wherein accm is an antigenicity conferring carrier material, and the spacer is —S—Y—, wherein S is attached to the accm or HRP and Y is a substituted or unsubstituted, straight or branched chain alkyl group of 1-10 carbon atoms.

Optionally, the immunogen has the general formula of Structure I; wherein R is selected from benzyl and isobutyl; each of X1 and X3 is a hydrogen atom (H); and X2 is [accm-spacer-], wherein accm is an antigenicity conferring carrier material, and the spacer is —S—CH$_2$—CH(NH$_2$)—C(O)—.

Optionally, the immunogen has the general formula of Structure I; wherein R is selected from benzyl and isobutyl; each of X1 and X3 is a hydrogen atom (H); and X2 is [accm-spacer-], wherein accm is an antigenicity conferring carrier material selected from the group consisting of keyhole limpet haemocyanin (KLH), bovine thyroglobulin (BTG), bovine serum albumin (BSA), egg ovalbumin, bovine gamma globulin, and cationised BSA, and the spacer is —S—CH$_2$—CH(NH$_2$)—C(O)—.

Optionally, the tracer has the general formula of Structure I; wherein R is selected from benzyl and isobutyl; X1, X2, and X3 are each independently selected from a hydrogen atom (H) and [HRP-spacer-], wherein HRP is horseradish peroxidase.

Optionally, the tracer has the general formula of Structure I; wherein R is selected from benzyl and isobutyl; each of X1 and X3 is a hydrogen atom (H); and X2 is [HRP-spacer-], wherein HRP is horseradish peroxidase.

Alternatively, the tracer has the general formula of Structure I; wherein R is selected from benzyl and isobutyl; each of X1 and X3 is a hydrogen atom (H); and X2 is [labelling agent-spacer-], wherein labelling agent is selected from the group consisting of an enzyme, a luminescent substance, a radioactive substance, and a mixture each thereof.

Optionally, the luminescent substance is selected from the group consisting of a bioluminescent, chemiluminescent, and fluorescent material.

Preferably, the labelling agent is an enzyme, preferably a peroxidase, most preferably horseradish peroxidase (HRP).

Optionally, the tracer has the general formula of Structure I; wherein R is selected from benzyl and isobutyl; each of X1 and X3 is a hydrogen atom (H); and X2 is [HRP-spacer-], wherein HRP is horseradish peroxidase, and spacer is selected from one or more of the group consisting of a substituted or unsubstituted alkyl group, a substituted or unsubstituted alkenyl group, a substituted or unsubstituted cycloalkyl group, a substituted or unsubstituted heterocyclyl group, a substituted or unsubstituted aryl group, and a substituted or unsubstituted heteroaryl group.

Optionally, the tracer has the general formula of Structure I; wherein R is selected from benzyl and isobutyl; each of X1 and X3 is a hydrogen atom (H); and X2 is [HRP-spacer-], wherein HRP is horseradish peroxidase, and spacer is —S—CH$_2$—CH(NH$_2$)—C(O)—.

According to a second aspect of the present invention, there is provided an antibody derivable from the immunogen according to the first aspect of the invention.

Optionally, the antibody is derived from the immunogen according to the first aspect of the invention.

Optionally, the antibody is derived from an immunogen having the general formula of Structure I; wherein R is selected from benzyl and isobutyl; X1, X2, and X3 are each independently selected from a hydrogen atom (H) and [accm-spacer-], wherein accm is an antigenicity conferring carrier material.

Optionally, the antibody is derived from an immunogen having the general formula of Structure I; wherein R is selected from benzyl and isobutyl; each of X1 and X3 is a hydrogen atom (H); and X2 is [accm-spacer-], wherein accm is an antigenicity conferring carrier material.

Optionally, the antibody is derived from an immunogen having the general formula of Structure I; wherein R is selected from benzyl and isobutyl; each of X1 and X3 is a hydrogen atom (H); and X2 is [accm-spacer-], wherein accm is an antigenicity conferring carrier material, and spacer is a substituted or unsubstituted, straight or branched chain alkyl group of 1-10 carbon atoms and having terminal heteroatoms, functional groups, or transformed functional groups.

Optionally, the antibody is derived from an immunogen having the general formula of Structure I; wherein R is selected from benzyl and isobutyl; each of X1 and X3 is a hydrogen atom (H); and X2 is [accm-spacer-], wherein accm is an antigenicity conferring carrier material, and the spacer is —S—Y—, wherein S is attached to the accm or HRP and Y is a substituted or unsubstituted, straight or branched chain alkyl group of 1-10 carbon atoms.

Optionally, the antibody is derived from an immunogen having the general formula of Structure I; wherein R is selected from benzyl and isobutyl; each of X1 and X3 is a hydrogen atom (H); and X2 is [accm-spacer-], wherein accm is an antigenicity conferring carrier material, and the spacer is —S—CH$_2$—CH(NH$_2$)—C(O)—.

Optionally, the antibody is derived from an immunogen having the general formula of Structure I; wherein R is selected from benzyl and isobutyl; each of X1 and X3 is a hydrogen atom (H); and X2 is [accm-spacer-], wherein accm is an antigenicity conferring carrier material selected from the group consisting of keyhole limpet haemocyanin (KLH), bovine thyroglobulin (BTG), bovine serum albumin (BSA), egg ovalbumin, bovine gamma globulin, and cationised BSA, and the spacer is —S—CH$_2$—CH(NH$_2$)—C(O)—.

Optionally, the antibody is capable of binding Colistin. Further optionally or additionally, the antibody is capable of binding Polymyxin B. Further optionally, the antibody is capable of binding Colistin and Polymyxin B.

Optionally, the antibody is capable of binding Colistin and Polymyxin B with sufficient sensitivity to enable a working assay. Further optionally, the antibody is capable of binding Colistin and Polymyxin B with sufficient sensitivity to enable a working assay in the presence of each or both of Colistin and Polymyxin B. Still further optionally, the antibody is capable of binding Colistin and Polymyxin B with sufficient sensitivity to enable a working assay in the presence of any or all of Colistin A, Colistin B, Polymyxin B1, and Polymyxin B2.

Optionally, the antibody is a polyclonal antibody. Alternatively, the antibody is a monoclonal antibody.

According to a further aspect of the present invention, there is provided a device for detecting polymyxins, the device comprising an antibody according to a second aspect of the present invention.

Optionally, the device comprises the antibody and a solid support. Further optionally, the device comprises the antibody attached to the solid support. Still further optionally, the device comprises the antibody irreversibly attached to the solid support. Still further optionally, the device comprises the antibody bonded to the solid support. Still further optionally, the device comprises the antibody irreversibly bonded to the solid support.

Optionally, the device comprises the antibody adsorbed to the solid support. Further optionally, the device comprises the antibody passively adsorbed to the solid support.

Optionally, the solid support is a solid state device. Optionally, the solid support is a solid state device selected from the group consisting of a biochip, a microtitre plate, a slide, a bead, a nanoparticle.

Optionally, the solid support is formed from a material selected from the group consisting of glass, plastic, and ceramic.

Optionally, the solid support further comprises at least one coating layer. Further optionally, the solid support further comprises a coating layer. Alternatively, the solid support further comprises two coating layers.

According to a still further aspect of the present invention, there is provided a method for detecting or determining polymyxins in a sample, the method comprising the steps of contacting the sample with an antibody according to a second aspect of the present invention, and detecting or determining any polymyxins in the sample bound to the antibody.

Optionally, the polymixins is one or both of Polymyxin B and Colistin, or a salt of each thereof. Further optionally, the polymixins or salt each thereof is one or both of Polymyxin B sulphate and trifluoroacetate.

Optionally, the method is a method of detecting or determining in a sample, a compound comprising Structure I wherein R is selected from the group consisting of benzyl and isobutyl, and X1, X2, and X3 are each independently selected from the group consisting of a hydrogen atom (H) and [alk-C(O)—] wherein alk is a substituted or unsubstituted, straight or branched chain alkyl group of 1-10 carbon atoms; the method comprising the steps of: contacting the sample with an antibody according to a second aspect of the present invention, and detecting or determining in the sample any compound comprising Structure I wherein R is selected from the group consisting of benzyl and isobutyl, and X1, X2, and X3 are each independently selected from the group consisting of a hydrogen atom (H) and [alk-C(O)—] wherein alk is a substituted or unsubstituted, straight or branched chain alkyl group of 1-10 carbon atoms, and which is bound to the antibody.

Optionally, the method is a method of detecting or determining in a sample, a compound comprising Structure I wherein R is selected from the group consisting of benzyl and isobutyl, and X1, X2, and X3 are each independently selected from the group consisting of a hydrogen atom (H) and [alk-C(O)—] wherein alk is 5-methylheptyl; the method comprising the steps of: contacting the sample with an antibody according to a second aspect of the present invention, and detecting or determining in the sample any compound comprising Structure I wherein R is selected from the group consisting of benzyl and isobutyl, and X1, X2, and X3 are each independently selected from the group consisting of a hydrogen atom (H) and [alk-C(O)—] wherein alk is 5-methylheptyl, and which is bound to the antibody.

Optionally, the method is a method of detecting or determining in a sample, a compound comprising Structure I wherein R is selected from the group consisting of benzyl and isobutyl, and X1, X2, and X3 are each independently selected from the group consisting of a hydrogen atom (H) and [alk-C(O)—] wherein alk is 5-methylhexyl; the method comprising the steps of: contacting the sample with an antibody according to a second aspect of the present invention, and detecting or determining in the sample any compound comprising Structure I wherein R is selected from the group consisting of benzyl and isobutyl, and X1, X2, and X3 are each independently selected from the group consisting of a hydrogen atom (H) and [alk-C(O)—] wherein alk is 5-methylhexyl, and which is bound to the antibody.

Optionally, the detecting or determining step further comprises contacting the sample with a tracer according to a first aspect of the present invention.

Optionally, the method comprises contacting the sample with an antibody according to a second aspect of the present invention and a tracer according to a first aspect of the present invention, and detecting or determining any polymyxins in the sample bound to the antibody.

Optionally, the method comprises contacting the sample with an antibody according to a second aspect of the present invention and a tracer according to a first aspect of the present invention, detecting or determining any tracer in the sample bound to the antibody, and detecting or determining any polymyxins in the sample bound to the antibody.

Optionally, the method comprises contacting the sample with an antibody according to a second aspect of the present invention and a tracer according to a first aspect of the present invention, detecting or determining any tracer in the sample bound to the antibody, and detecting or determining any polymyxins in the sample bound to the antibody from the presence of any tracer in the sample.

Optionally, detecting or determining any tracer in the sample bound to the antibody comprises detecting or determining a signal emitted by the tracer.

Optionally or additionally, detecting or determining any polymyxins in the sample bound to the antibody from the presence of any tracer in the sample comprises determining the magnitude of the signal emitted by the tracer comparing the magnitude of the signal emitted by the tracer to a calibrator or calibrator value.

Optionally or additionally, detecting or determining any polymyxins in the sample bound to the antibody from the presence of any tracer in the sample further comprises confirming the presence or absence of, or deriving the concentration of, any polymyxins in the sample from the comparison of the magnitude of the signal emitted by the tracer to the calibrator or calibrator value.

Optionally, the sample is an in vitro sample.

Optionally, the sample is a solution.

Optionally, the sample is selected from the group consisting of a blood sample, a urine sample, a milk sample, a meat sample, and a fish produce sample.

According to a still further aspect of the present invention, there is provided a kit for detecting or determining polymyxins in a sample, the kit comprising at least one antibody according to the second aspect of the present invention.

Optionally or additionally, the kit comprises instructions for use.

Optionally, the kit comprises at least one device according to the further aspect of the present invention.

Optionally, the kit comprises at least one tracer according to a first aspect of the present invention.

BRIEF DESCRIPTION OF THE DRAWINGS

Embodiments of the present invention will be described with reference to the following non-limiting examples and the accompanying drawings, in which.

DETAILED DESCRIPTION OF THE INVENTION

The present invention describes a hapten, immunogen, and/or tracer of Structure I:

Structure I in which R can be either benzyl or isobutyl; two of X1, X2, and X3 can be H, and the other can be:
- for the hapten: SH—Z—, in which Z can be a straight chain or substituted straight chain or branched alkyl group, preferably of 1-10 carbon atoms;
- for the immunogen: accm-spacer-, where accm can be an antigenicity conferring carrier material; and
- for the tracer: HRP-spacer-, where HRP can be horseradish peroxidase.

Preferably, for each of the immunogen, hapten and tracer, X1 and X3 can be H.

The hapten preferably can be X1 and X3=H, and X2 can be HS—CH2-CH(NH2)-C(O)—.

The spacer can be any group which facilitates the bonding of the Polymyxin to the accm/HRP. The term 'Polymyxin' can mean both Polymyxin B and Colistin. The spacer can act as a bridge between the accm/HRP and the Polymyxin and can be any suitable spacing group known in the art (e.g. Thermo Scientific Crosslinking Technical Handbook, 1606073 April 2009; Bioconjugate Techniques G. Hermanson, ed, Academic Press, 1996, 785 pp, which describes both spacers and accms, and is incorporated herein in its entirety). For example, the spacer can be various combinations of one or more of substituted or unsubstituted alkyl, alkenyl, cycloalkyl, heterocyclyl, aryl, heteroaryl. Prior to its bonding to the Polymyxin and accm/HRP, it commonly has terminal heteroatoms or functional groups to facilitate the bonding. Following bonding, the heteroatom or a transformed functional group often remains. The spacer can be preferably a straight chain or substituted straight chain or branched alkyl group, preferably of 1-10 carbon atoms, with terminal heteroatoms or functional or transformed functional groups. The spacer can preferably incorporate a thiol group. In a preferred embodiment, the immunogens and tracers of the invention are of Structure I in which the spacer is —S—Y— (S attached to the accm/HRP), in which Y is a straight chain or substituted straight chain or branched alkyl group, preferably of 1-10 carbon atoms, with a terminal heteroatom or functional or transformed functional groups. An example of a spacer of the invention for both the immunogen and tracer is —S—CH2-CH(NH2)-C(O)— i.e. Y is —CH2-CH(NH2)-C(O)—.

The accm can be a macromolecule which promotes immunogenicity. Appropriate accms can contain poly(amino acid) segments and include polypeptides, proteins, and protein fragments. Illustrative examples of antigencity conferring carrier materials of the invention are keyhole limpet haemocyanin (KLH), bovine thyroglobulin (BTG), bovine serum albumin (BSA), egg ovalbumin, bovine gamma globulin, and cationised BSA. Alternatively, synthetic poly (amino acids) having a sufficient number of available amino groups, such as lysine, can be employed, as can other synthetic or natural polymeric materials bearing reactive functional groups. Also, carbohydrates, yeasts, or polysaccharides can be conjugated to the hapten to produce an immunogen. To facilitate or to ensure bonding of the accm/HRP to the spacer, chemically active groups can be introduced into the accm. For example, activation of a protein such as HRP, BTG, BSA or KLH with maleimide makes such a product reactive to thiol groups. Therefore, a spacer with a thiol group incorporated can be bonded to a HRP or a proteinaceous accm by activation with a maleimide group. Hence, the accm/HRP as described in the immunogens and tracers of the invention can also be activated i.e. they can incorporate an activation group prior to their bonding to the spacer.

The presence of multiple amino acid groups within Polymyxin B and Colistin requires a targeted synthetic method if a single point of derivatisation is required when forming the hapten. The hapten represents a pre-immunogenic molecule which is subsequently bonded to the accm, resulting in immunogen formation. The hapten or accm is preferentially activated prior to immunogen formation.

Figure 1:
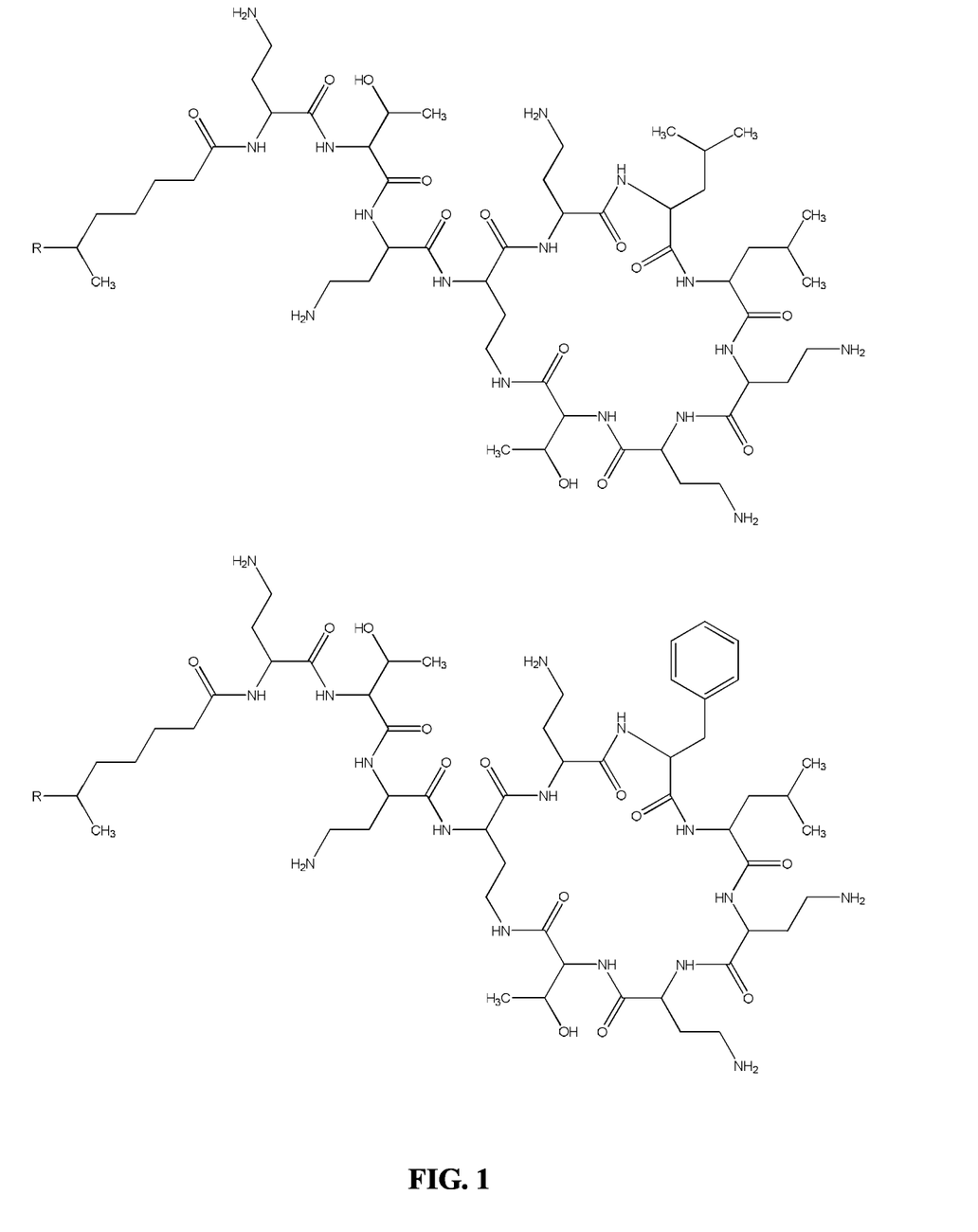
FIG. 1 illustrates Polymyxin B and Colistin (R=Me, Et)
Figure 2:
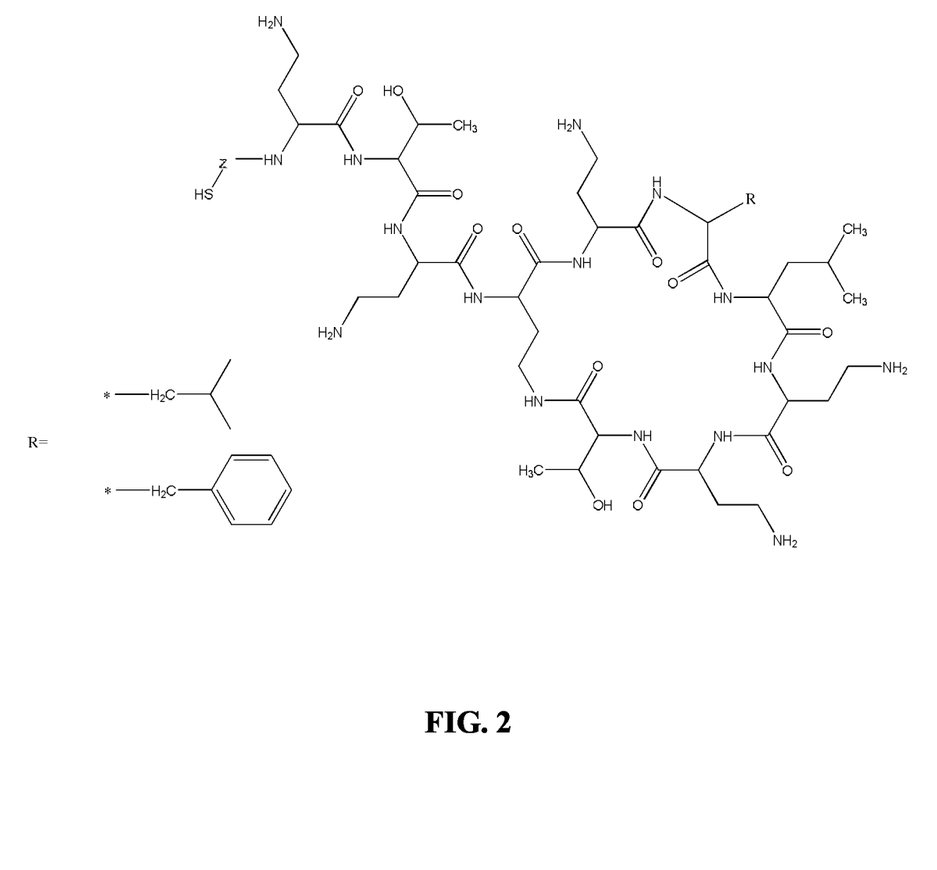
FIG. 2 illustrates haptens of Polymyxin B and Colistin according to the invention.
Figure 3:
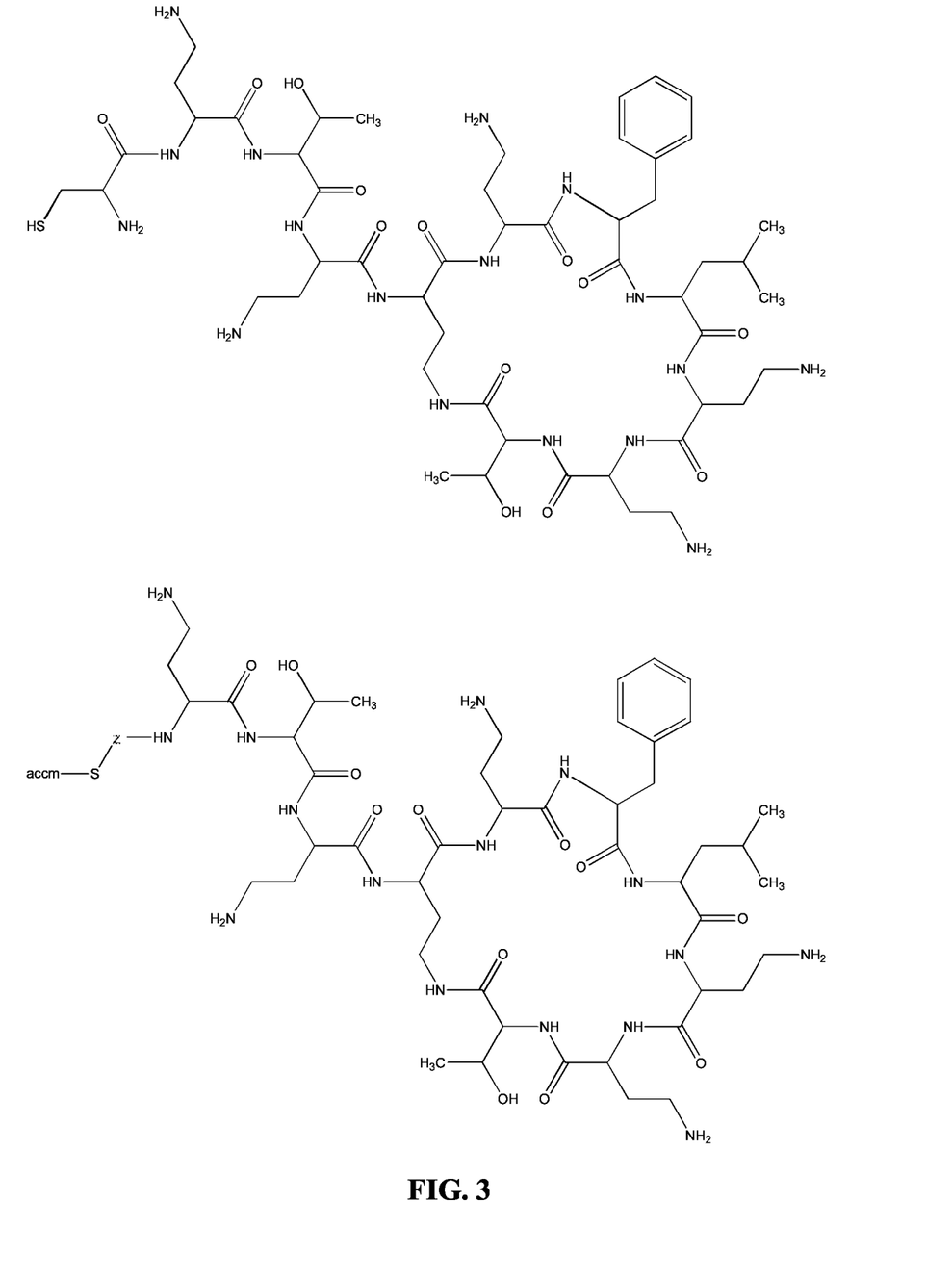
FIG. 3 illustrates Polymyxin B hapten (top) and Polymyxin B immunogen (bottom) according to the invention.
Figure 4:
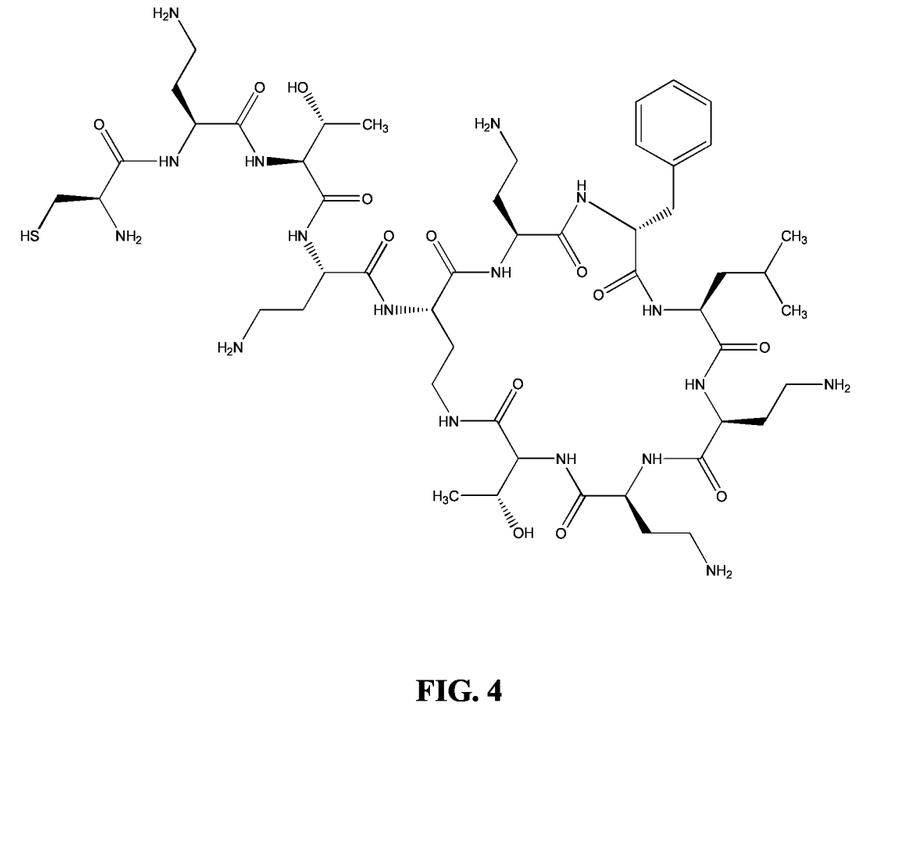
FIG. 4 illustrates a stereospecific Polymyxin B hapten according to the invention.

Unless otherwise stated, the individual polymyxin compounds described herein include all possible stereochemical forms including racemates, enantiomers, and diastereomers. For example, the Polymyxin hapten of FIG. 2 (top) incorporates the compounds of FIG. 4 (the stereospecific compound).

There are various possible synthetic methods for preparing haptens of the invention, including building up the haptens from individual amino acid groups using solid phase peptide synthesis in conjunction with tBoc (tert-butyl-oxycarbonyl) or fMoc (fluorenylmethyloxycarbonyl). Alternatively, a polymyxin compound can be sourced commercially and subjected to protection followed by deacylation of the tail group, deprotection, and subsequent derivatisation. If the commercially sourced polymyxin is a mixture of components, an individual component can be isolated by a suitable separation method such as preparative high resolution liquid chromatography and then suitably derivatised.

The invention further describes an antibody derived from an immunogen of the invention. Preferably, the antibody is derived from an immunogen of Structure I in which $X_2$ is the point of derivatisation. The antibody of the invention surprisingly binds with sufficient sensitivity to both Colistin and Polymyxin B to enable a working assay whether Colistin and Polymyxin B exist as single compounds or mixtures of Colistin A, Colistin B, Polymyxin B1 and Polymyxin B2. Sensitivity of antibody-ligand binding is calculated using a recognised metric such as the IC50. The antibodies can be monoclonal or polyclonal antibodies.

In a preferred embodiment, the antibody is passively adsorbed on or bonded, for example by covalent bonds, to the surface of a solid state device such as a biochip, a microtitre plate, a glass slide, a bead etc. The solid state device represents a solid substrate with which the Polymyxin antibody is associated. A possible problem associated with placing Polymyxin antigen onto the solid state device surface is the presence of bacterial lipopolysaccharide (LPS) in the sample to be measured. As Polymyxins are known to bind to LPS, either masking of plate-bound antigen from the solution antibody or for non-covalently bound antigen, desorption of antigen, could occur. By placing the Polymyxin antibody on the solid state device possible problems caused by potential bacterial lipopolysaccharides are avoided. Covalent bonding generally requires the initial introduction of a chemically active compound covalently attached to the substrate surface prior to antibody addition. The antibody itself may also require the addition of a chemical activating group to achieve substrate bonding. These requirements are well known in the art.

The substrate can be any medium capable of adsorbing or bonding to an antibody, for example a bead or nanoparticle (optionally chemically-activated), but is preferably of a planar conformation (optionally chemically-activated) such as a biochip. A biochip is a thin, wafer-like substrate with a planar surface which can be made of any suitable material such as glass or plastic but is preferably made of ceramic. The biochip is able to be chemically-activated prior to antibody bonding or is amenable to the passive adsorption of antibodies. The skilled person in biochip development for immunoassay application will recognize that a planar surface at high resolution e.g. if using a scanning electron microscope, is not perfectly 'flat' but will possess an uneven surface. The important aspect being that the 'approximately' planar surface is suitable for application. A microlayer coating of material can optionally be added to the planar surface of the substrate prior to antibody placement. Either the upper surface or both surfaces of the substrate can be coated. The chip can be integrated into or placed into a device with walls. Such a walled device can aid in the retention of added sample or solution.

The solid state device can also support other antibodies which have a binding specificity which is different from the binding specificity of the antibodies of the invention. Such a support with multiple different antibodies is often described as a multianalyte array. Reference to an 'array' includes a microarray. If the method of detection is different fluorescent labels, each different fluorescent label emitting electromagnetic radiation at a unique wavelength, then the location of placement of the antibodies on the solid substrate is not critical.

However, for antibodies forming part of a multianalyte array in which the detectable label is, for example, a chemiluminescent molecule, the antibodies of differing specificity must not overlap and must be located in discrete areas on the solid state device. Such a system is also referred to as a spatially addressable multianalyte array.

The invention also describes a method of detecting or determining a compound comprising Structure II in an in vitro sample or in a solution comprising contacting the sample or solution with a detecting agent and an antibody of the invention, detecting the bound detecting agent and deducing the presence of a compound comprising structure II:

Structure II in which R is either benzyl or isobutyl; and two of X1, X2, and X3 are H, and the other is alk-C(O)—; the method comprising contacting the sample with an antibody of the invention and a tracer of the invention, detecting a signal emitted by the tracer and based on the magnitude of a detected signal or the lack of a signal with reference to a calibrator value, confirming the presence or absence of, or deriving the concentration of, the Polymyxin.

Alk can be C1-10 straight or branched carbon chain. Preferably X1 and X3 are each H and alk is 5-methylheptyl or 5-methylhexyl.

The method is particularly suitable for the detection and determination of Polymyxin B and Colistin. The method is suitable for detecting the corresponding Polymyxin salts, such as Polymyxin B sulphate or trifluoroacetate.

Suitable samples for detection include blood, urine, milk, meat and fish produce. The samples may require a pre-treatment step to make them suitable for testing.

By 'detecting' is meant qualitatively analysing for the presence or absence of a substance. By 'determining' is meant quantitatively analysing for the amount of a substance present.

The detection or determination step is usually effected with the aid of a calibrator. A calibrator is well known in the art and refers to a reference value or values, the reference being a substance which enables a threshold concentration or the exact or calibrator equivalent amount of analyte(s) to be determined. The determination of an exact or calibrator equivalent amount of analyte(s) usually requires the construction of a calibration curve (also known as a standard curve). The number of calibrator points can vary, but is usually from 5 to 9. Calibrator values can be generated in situ or may be derived from previously generated values.

To enable a practical assay for clinical/commercial use, the binding of the antibody to the analyte(s) must be such that the concentration at which the analytes are detected or determined is at an acceptable level. The detecting agent (also known as a tracer) is the substance which emits a detectable signal and comprises a moiety of similar structure to a target analyte conjugated, by way of the spacer, to a labelling agent, that is able to bind to one of the antibodies of the invention. The tracer structure preferably comprises a tracer derived from either Example 7 or 8.

The labelling agent, a component which is standard in the art, is selected from an enzyme, a luminescent substance, a radioactive substance, or a mixture thereof. Preferably, the labelling agent is an enzyme, preferably a peroxidase, most preferably horseradish peroxidase (HRP). Alternatively, or additionally, the luminescent substance may be a bioluminescent, chemiluminescent or fluorescent material.

The invention further describes a kit comprising an antibody of the invention which is preferably adsorbed on or bonded to a solid state device. The solid state device is preferably a biochip (which is preferably ceramic) or a microtitre plate. The kit optionally includes a tracer of the invention.

General Methods, Examples and Results
Preparation of Haptens

For both the Polymyxin B and Colistin based haptens, the linear peptide was synthesised using classical solid-phase, Fmoc/tBu methods on an acid sensitive polystyrene based resin. The γ-NH2 protecting group of the Dab5 residue was selectively removed and, in the same reaction, the partially protected linear peptide was cleaved from the resin. The peptide was cyclised in solution, semi-purified by reverse phase HPLC and globally deprotected. The final product was then further purified by reverse phase HPLC to give the hapten.

Preparation of Immunogens and Detecting Agents

In immunology, haptens are defined as substances which by themselves cannot elicit immune responses. They require chemical coupling to larger immunogenic molecules (antigenicity conferring carrier materials or 'accm'), to be capable of inducing an immune response. Appropriate accms commonly contain poly(amino acid) segments and include polypeptides, proteins and protein fragments. Illustrative examples of antigencity conferring carrier materials are keyhole limpet haemocyanin (KLH), bovine thyroglobulin (BTG), bovine serum albumin (BSA), egg ovalbumin, bovine gamma globulin or cationised BSA. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Conjugation of haptens can be performed using standard methods of conjugation such as mixed anhydride, EDC or succinimidyl activation of the haptens. In order to confirm that adequate conjugation of hapten to accm has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

Preparation of Antisera

In order to generate polyclonal antisera, 2 mg of an immunogen of the present invention is prepared in PBS, mixed at a ratio of 50% immunogen in PBS with 50% Freund's Complete adjuvant (Sigma, Product Number—F5881) and emulsified by repeatedly passing the mixture through a tip on the end of a 1 ml syringe, until it reaches the required semi-solid consistency. 1 ml of the mixture is then injected into a host animal, such as rabbit, sheep, mouse, guinea pig or horse. Sheep are the preferred host animal. Further injections (boosts) are administered on a monthly basis (1 mg of immunogen is prepared in PBS and mixed at a ratio of 50% immunogen in PBS with 50% of Freund's Incomplete Adjuvant, Sigma product Number—F5506) until the required titre is achieved. Serum is sampled for evaluation of the antibody titre. Briefly, blood is collected by applying pressure to the exposed jugular vein and inserting a clean 14 gauge hypodermic needle to remove 500 ml of blood per sheep, under gravity. The blood is stored at 37° C. for a minimum of 1 hour before the clots are separated from the side of the centrifuge bottles using disposable 1 ml pipettes (ringing). The samples are stored at 4° C. overnight. Samples are then centrifuged at 4200 rpm for 30 minutes at 4° C. The serum is poured off and centrifuged again, at 10,000 rpm for 15 minutes at 4° C., before being aliquoted and stored at <−20° C. The Immunoglobulin (Ig) fraction is extracted from the antisera via caprylic acid/ammonium sulphate precipitation of immunoglobulin.

The antibody titre is evaluated by coating a microtitre plate (Thermo Fisher Scientific NUNC, 468667) with antibody (125 µl/well) in coating buffer (10 mM Tris pH 8.5) at 37° C. for 2 hours. The plate is then washed 4 times over 10 minutes with working strength TBST. 50 µl of sample/standard is added to the appropriate wells in triplicate, followed by 75 µl of hapten-HRP conjugate and incubated at 25° C. for 1 hour. The plate is then washed and 125 µl of TMB (Randox Laboratories, 4380-15) added to each well and left at room temperature for 20 mins in the dark. The reaction is stopped using 125 µl of 0.2 M sulphuric acid. The absorbances are read at 450 nm with an ELISA microplate reader (BIO-TEK Instruments, Elx800) and the means calculated. Antibody sensitivity can then be determined. When the optimal titre has been attained, the host animal is bled to yield a suitable volume of specific antiserum (overall this results in 20 bleeds in total, with approximately 200 ml of antiserum achieved per bleed). The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Various purification steps are available if required, including Immunoglobulin Precipitation (as described above), Antigen-specific affinity purification, Size-exclusion chromatography and Ion Exchange Chromatography.

Immunoassay Development

The process of developing an immunoassay is well known to the person skilled in the art. Briefly, for a competitive immunoassay in which the target analyte is a non-immunogenic molecule such as a hapten, a general immunoassay development process outlined. Following antibody production, a detecting agent is added to a sample containing the target analyte and the raised antibodies, and the detecting agent and analyte compete for binding to the antibodies. The process may comprise fixing said serum antibodies to a solid state device such as a polystyrene support or a ceramic chip. The antibodies can be polyclonal or monoclonal using standard techniques, but the current invention makes use of polyclonal antibodies. The signal emitted in the immunoassay is proportionate to the quantity of detecting agent bound to the antibodies which in turn is inversely proportionate to the analyte concentration. The signal can be detected or quantified by comparison with a calibrator.

Polymixin B BSA Immunogen—Thio-maleimide Method
Preparation of Carrier Protein

4-N-Maleimidomethylcyclohexyl-1-carboxylic acid NHS ester solution (2.06 mg) in N,N-Dimethylformamide (0.034 mL) was added drop-wise to 5 mg BSA solution (pH8.0) while stirring. And then the resulting solution was rolled at 15-25° C. for 16-20 hours. Excess 4-N-Maleimidomethylcyclohexyl-1-carboxylic acid NHS ester was removed by dialysis at 2-8° C. against Phosphate Buffered Saline, pH 7.2.

Conjugation (Des-6-methyloctanoyl,Cys$^0$)-Polymyxin $B_1$ trifluoroacetate salt (1.68 mg) dissolved in Phosphate Buffered Saline, pH 7.2 with 10 mM EDTA was added to the modified carrier protein, rolled for 16-20 hours at +15 to +25° C., and then L-Cysteine (0.45 mg) dissolved in double de-ionised water was added, rolled for 2 hours at +15 to +25° C. Excess hapten was removed by dialysis at 2-8° C. against Phosphate Buffered Saline, pH 7.2.

Polymixin B KLH Immunogen—Thio-maleimide Method
Preparation of Carrier Protein

4-N-Maleimidomethylcyclohexyl-1-carboxylic acid NHS ester solution (41.13 mg) in N,N-Dimethylformamide (0.685 mL) was added drop-wise to 100 mg KLH solution (pH8.0) while stirring. And then the resulting solution was rolled at 15-25° C. for 16-20 hours. Excess 4-N-Maleimidomethylcyclohexyl-1-carboxylic acid NHS ester was removed by dialysis at 2-8° C. against Phosphate Buffered Saline, pH 7.2.

Conjugation (Des-6-methyloctanoyl,Cys$^0$)-Polymyxin $B_1$ trifluoroacetate salt (33.6 mg) dissolved in Phosphate Buffered Saline, pH 7.2 with 10 mM EDTA was added to the modified carrier protein, rolled for 16-20 hours at +15 to +25° C., and then L-Cysteine (9.08 mg) dissolved in double de-ionised water was added, rolled for 2 hours at +15-+25° C. Excess hapten was removed by dialysis at 2-8° C. against Phosphate Buffered Saline, pH 7.2.

Polymixin B HRP Tracer—Thio-maleimide Method
Preparation of HRP

4-N-Maleimidomethylcyclohexyl-1-carboxylic acid NHS ester solution (0.375 mg) in N,N-Dimethylformamide (0.02 mL) was added drop-wise to HRP (10 mg) dissolved in 50 mM HEPES solution, pH8.5 (0.4 mL) while stirring. And then the resulting solution was rolled at 15-25° C. for 40 minutes. Excess 4-N-Maleimidomethylcyclohexyl-1-carboxylic acid NHS ester was removed by dialysis against Phosphate Buffered Saline, pH 7.2. Keep the solution darkened during the processing.

Preparation of Hapten (Des-6-methyloctanoyl,Cys$^0$)-Polymyxin $B_1$ trifluoroacetate salt (1 mg) was dissolved in in Phosphate Buffered Saline, pH 7.2 with 10 mM EDTA (0.1 mL).

Conjugation

The modified HRP was added to the hapten, rolled for 16-20 hours at +15 to +25° C. Excess hapten was removed with PD-10 column (Pharmacia), pre-equilibrated with Phosphate Buffered Saline, pH 7.2, followed by vivaspin 6 centrifugal concentrators. The solution was kept darkened during the processing.

Polymixin B HRP Tracer—Thio-maleimide Method
Preparation of HRP

4-N-Maleimidomethylcyclohexyl-1-carboxylic acid NHS ester solution (0.375 mg) in N,N-Dimethylformamide (0.02 mL) was added drop-wise to HRP (10 mg) dissolved in 50 mM HEPES solution, pH8.5 (0.4 mL) while stirring. And then the resulting solution was rolled at 15-25° C. for 40 minutes. Excess 4-N-Maleimidomethylcyclohexyl-1-carboxylic acid NHS ester was removed by dialysis against Phosphate Buffered Saline, pH 7.2. The solution was kept darkened during the processing.

Preparation of Hapten (Des-6-methyloctanoyl,Cys$^0$)-Polymyxin $B_1$ trifluoroacetate salt (1 mg) was dissolved in Phosphate Buffered Saline, pH 7.2 with 10 mM EDTA (0.1 mL). TCEP.HCl solution (2.5 L at 100 mg/mL ddH2O) was added, and rolled at 15-25° C. for 2 hours. Excess TCEP.HCl was removed with Spin desalting column pre-equilibrated with Phosphate Buffered Saline, pH 7.2 with 10 mM EDTA.

Conjugation

The modified HRP was added to the activated hapten, rolled for 16-20 hours at +15 to +25° C. Excess hapten was removed with PD-10 column (Pharmacia), pre-equilibrated with Phosphate Buffered Saline, pH 7.2, followed by vivaspin 6 centrifugal concentrators. The solution was kept darkened during the processing.

Polymixin B HRP Tracer—Thio-maleimide Method
Preparation of HRP

2-Iminothiolane hydrochloride solution (0.27 mL at 10 mg/mL Phosphate Buffered Saline, pH 7.2 with 10 mM EDTA) was added drop-wise to HRP (20 mg) dissolved in Phosphate Buffered Saline, pH 7.2 with 10 mM EDTA (1.0 mL) while stirring. And then the resulting solution was rolled at 15-25° C. for 16-20 hours. Excess 2-Iminothiolane hydrochloride was removed with PD-10 column (Pharmacia), pre-equilibrated with Phosphate Buffered Saline, pH 7.2 with 10 mM EDTA. The solution was kept darkened during the processing.

Conjugation

The modified HRP was added to Polymixin B Sulfate (10 mg), and 4-N-malemido phenyl butyric acid NHS solution (40 L at 100 mg/mL DMF) was added, and then rolled for 16-20 hours at +15 to +25° C. N-Ethylmaleimide solution (40 µL at 50 mg/mL DMF) was added, and then rolled for 2 hours at +15 to +25° C. Excess hapten was removed with PD-10 column (Pharmacia), pre-equilibrated with Phosphate Buffered Saline, pH 7.2, followed by dialysis at 2-8° C. against Phosphate Buffered Saline, pH 7.2. Keep the solution darkened during the processing.

Colistin HRP Tracer—Thio-maleimide Method
Preparation of HRP

4-N-Maleimidomethylcyclohexyl-1-carboxylic acid NHS ester solution (0.375 mg) in N,N-Dimethylformamide (0.02 mL) was added drop-wise to HRP (10 mg) dissolved in 50 mM HEPES solution, pH8.5 (0.4 mL) while stirring. And then the resulting solution was rolled at 15-25° C. for 40 minutes. Excess 4-N-Maleimidomethylcyclohexyl-1-carboxylic acid NHS ester was removed by dialysis against Phosphate Buffered Saline, pH 7.2. The solution was kept darkened during the processing.

Preparation of Hapten (Des-6-methyloctanoyl,Cys$^0$)-Colistin A trifluoroacetate salt (1 mg) was dissolved in in Phosphate Buffered Saline, pH 7.2 with 10 mM EDTA (0.1 mL).

Conjugation

The modified HRP was added to the hapten, rolled for 16-20 hours at +15 to +25° C. Excess hapten was removed with PD-10 column (Pharmacia), pre-equilibrated with Phosphate Buffered Saline, pH 7.2, followed by vivaspin 6 centrifugal concentrators. Keep the solution darkened during the processing.

Colistin HRP Tracer—Thio-maleimide Method
Preparation of HRP

4-N-Maleimidomethylcyclohexyl-1-carboxylic acid NHS ester solution (0.375 mg) in N,N-Dimethylformamide (0.02 mL) was added drop-wise to HRP (10 mg) dissolved in 50 mM HEPES solution, pH8.5 (0.4 mL) while stirring. And then the resulting solution was rolled at 15-25° C. for 40 minutes. Excess 4-N-Maleimidomethylcyclohexyl-1-carboxylic acid NHS ester was removed by dialysis against Phosphate Buffered Saline, pH 7.2. The solution was kept darkened during the processing.

Preparation of Hapten (Des-6-methyloctanoyl,Cys$^0$)-Colistin A trifluoroacetate salt (1 mg) was dissolved in Phosphate Buffered Saline, pH 7.2 with 10 mM EDTA (0.1 mL). TCEP.HCl solution (2.5 µL@ 100 mg/mL ddH2O) was added, and rolled at 15-25° C. for 2 hours. Excess TCEP.HCl was removed with Spin desalting column pre-equilibrated with Phosphate Buffered Saline, pH 7.2 with 10 mM EDTA.

Conjugation

The modified HRP was added to the activated hapten, rolled for 16-20 hours at +15 to +25° C. Excess hapten was removed with PD-10 column (Pharmacia), pre-equilibrated with Phosphate Buffered Saline, pH 7.2, followed by vivaspin 6 centrifugal concentrators. Keep the solution darkened during the processing.

Colistin HRP Tracer—Thio-maleimide Method
Preparation of HRP

2-Iminothiolane hydrochloride solution (0.27 mL at 10 mg/mL Phosphate Buffered Saline, pH 7.2 with 10 mM EDTA) was added drop-wise to HRP (20 mg) dissolved in Phosphate Buffered Saline, pH 7.2 with 10 mM EDTA (1.0 mL) while stirring. And then the resulting solution was rolled at 15-25° C. for 16-20 hours. Excess 2-Iminothiolane hydrochloride was removed with PD-10 column (Pharmacia), pre-equilibrated with Phosphate Buffered Saline, pH 7.2 with 10 mM EDTA. The solution was kept darkened during the processing.

Conjugation

The modified HRP was added to Colistin Sulfate (10 mg), and 4-N-malemido phenyl butyric acid NHS solution (40 µL at 100 mg/mL DMF) was added, and then rolled for 16-20 hours at +15 to +25° C. N-Ethylmaleimide solution (40 µL at 50 mg/mL DMF) was added, and then rolled for 2 hours at +15 to +25° C. Excess hapten was removed with PD-10 column (Pharmacia), pre-equilibrated with Phosphate Buffered Saline, pH 7.2, followed by dialysis at 2-8° C. against Phosphate Buffered Saline, pH 7.2. The solution was kept darkened during the processing.

General Method of Antibody Characterisation

175 µl of assay diluent, then 25 µl of Polymyxin diluted in calibrator base was added to the appropriate wells. Biochips spotted with antibody of the invention were incubated for 30 min at 25° C. in a thermo-shaker at 370 rpm. 100 µl Tracer of the invention was added to the appropriate wells. Biochips were incubated for 60 min at 25° C. in a thermo-shaker at 370 rpm. Biochips were washed with TBST (2 quick washes followed by 4 washes at 2 min intervals). Biochips were developed with 250 µl signal: peroxide (1:1) for 2 min in the dark. Biochips were imaged on the Randox Investigator (2×60 sec images). All biochips were manually processed.

TABLE 1

Standard curves for Polymyxin B and Colistin in relation to Polymyxin B derived antibody and Colistin-based tracer.

| Polymyxin B | | | Colistin | | |
|---|---|---|---|---|---|
| Standard conc$^n$ (ng/ml) | RLU | B/Bo | Standard conc$^n$ (ng/ml) | RLU | B/Bo |
| 0.00 | 8544 | 100 | 0.000 | 9192 | 100 |
| 0.078 | 7380 | 86 | 0.391 | 6524 | 71 |
| 0.156 | 6651 | 78 | 0.781 | 5297 | 58 |
| 0.313 | 5449 | 64 | 1.563 | 4046 | 44 |
| 0.625 | 4771 | 56 | 3.125 | 3034 | 33 |
| 1.250 | 4327 | 51 | 6.250 | 1586 | 17 |
| 2.500 | 3275 | 38 | 12.500 | 1029 | 11 |
| 5.000 | 2307 | 27 | 25.000 | 799 | 9 |
| 10.000 | 1400 | 16 | 50.000 | 574 | 6 |
| IC50 | 0.931 ng/ml (CR = 100%) | | | 1.191 ng/ml (CR = 80%) | |

RLU = relative light units
B = absorbance at 450 nm at xng/ml standard concentration
B$_0$ = absorbance at 450 nm at 0 ng/ml standard concentration
Percentage B/B0 = (B/B0) × 100
IC$_{50}$ = standard concentration which produces 50% inhibition of maximal signal
CR = percentage cross-reactivity

TABLE 2

Relative % Cross-reactivities of Polymyxin B-KLH derived antibody to Colistin and Polymyxin B, at different antibody concentrations and different tracer concentrations (Tracer is Colistin-HRP).

| Tracer dilution | Antibody RS2790 | | | | Antibody RS2801 | | | | Antibody RS2830 | | | |
|---|---|---|---|---|---|---|---|---|---|---|---|---|
| | 0.1 mg/ml | | 0.75 mg/ml | | 0.1 mg/ml | | 0.75 mg/ml | | 0.1 mg/ml | | 0.75 mg/ml | |
| | Col | Poly | Col | Poly | Col | Poly | Col | Poly | Col | Poly | Col | Poly |
| 1/50K | 5 | 100 | 8 | 100 | | | | | | | | |
| 1/100K | 23 | 100 | 59 | 100 | | | | | | | | |
| 1/500K | | | | | 20 | 100 | 67 | 100 | 6 | 100 | 8 | 100 |
| 1/1000K | | | | | 15 | 100 | 62 | 100 | 5 | 100 | 9 | 100 |

TABLE 3

Relative Binding (IC50 ng/ml) of different Polymyxin B-KLH derived antibodies to Colistin and Polymyxin B, at different antibody concentrations and different tracer concentrations.

| Tracer dilution | Antibody RS2790 | | | | Antibody RS2801 | | | | Antibody RS2830 | | | |
|---|---|---|---|---|---|---|---|---|---|---|---|---|
| | 0.1 mg/ml | | 0.75 mg/ml | | 0.1 mg/ml | | 0.75 mg/ml | | 0.1 mg/ml | | 0.75 mg/ml | |
| | Col | Poly | Col | Poly | Col | Poly | Col | Poly | Col | Poly | Col | Poly |
| 1/50K | 3.02 | 0.14 | 1.72 | 0.14 | | | | | | | | |
| 1/100K | 1.60 | 0.37 | 1.01 | 0.59 | | | | | | | | |
| 1/500K | | | | | 0.47 | 0.09 | 0.24 | 0.16 | 2.54 | 0.15 | 2.16 | 0.17 |
| 1/1000K | | | | | 0.78 | 0.12 | 0.22 | 0.13 | 3.62 | 0.17 | 2.47 | 0.22 |

Several different antibody-tracer combinations enable assays of high sensitivity to both Colistin and Polymyxin B. It is highly likely that other polymyxins with different hydrophobic tails will be susceptible to binding by the antibody of the invention increasing the scope of the assay.

Accordingly, the invention relates to haptens, immunogen and tracers of structure I in which R is either benzyl or isobutyl; two of $X_1$, $X_2$, and $X_3$ are H and the other is for the hapten SH—X— in which X is a straight chain or substituted straight chain or branched alkyl group, preferably of 1-10 carbon atoms, for the immunogen accm-spacer-where accm is an antigenicity conferring carrier material, for the tracer HRP-spacer where HRP is horseradish peroxidase.

structure I

Also disclosed is a hapten of the invention in which $X_1$ is —$CH_2$—$CH(NH_2)$—$C(O)$— in which the —$CH_2$— moiety is attached to the terminal thiol group.

Also disclosed is an immunogen of the invention in which the spacer is —S—Y—, in which S is attached to the accm preferably by an activating group and in which Y is a straight chain or substituted straight chain or branched alkyl group, preferably of 1-10 carbon atoms, optionally with a terminal heteroatom or functional group.

Also disclosed is a tracer of the invention in which the spacer is —S—Y—, in which S is attached to HRP preferably by an activating group and in which Y is a straight chain or substituted straight chain or branched alkyl group, preferably of 1-10 carbon atoms, optionally with a terminal heteroatom or functional group.

Also disclosed is an immunogen of the invention in which Y is —$CH_2$—$CH(NH_2)$—$C(O)$—in which the —$CH_2$— moiety is attached to the S atom and the activating group comprises a maleimidyl moiety.

Also disclosed is a tracer of the invention in which Y is —$CH_2$—$CH(NH_2)$—$C(O)$—in which the —$CH_2$— moiety is attached to the S atom and the activating group comprises a maleimidyl moiety.

Also disclosed is an antibody derived from an immunogen of the invention.

Also disclosed is an antibody of the invention which cross-reacts with Colistin and Polymyxin B.

Also disclosed is an antibody of the invention which is adsorbed on or bonded to the surface of a solid state device.

Also disclosed is an antibody of the invention in which the solid state device is a biochip or microtitre plate.

Also disclosed is a kit comprising an antibody of the invention.

Also disclosed is a method of detecting or determining a Polymyxin of structure II in a sample in which R is either benzyl or isobutyl and two of $X_1$, $X_2$, and $X_3$ are H and the other is alk-C(O)—, comprising contacting the sample with an antibody of the invention and a tracer of the invention, detecting a signal emitted by the tracer and based on the magnitude of a detected signal or the lack of a signal with reference to a calibrator value, confirming the presence or absence of, or deriving the concentration of, the Polymyxin.

Also disclosed is method of the invention in which $X_1$ and $X_3$ are H.

Also disclosed is a method of the invention in which alk is 5-methylheptyl or 5-methylhexyl.

Also disclosed is a method of the invention in which the Polymyxin is Polymyxin B and/or Colistin.

The invention claimed is:

1. A polyclonal antibody raised against an immunogen having the structure

Structure I structure II

-continued wherein Z is —CH$_2$—CH(NH$_2$)—C(O)—, wherein the accm includes keyhole limpet haemocyanin activated with N-succinimidyl 4-(maleimidomethyl)cyclohexanecarboxylate, wherein the polyclonal antibody binds specifically to Colistin and Polymyxin B, wherein the polyclonal antibody has a cross-reactivity of 100% to Polymyxin B and 80% to Colistin, wherein the cross-reactivity is measured in the presence of a tracer; and wherein the tracer is a conjugate of horseradish peroxidase activated with N-succinimidyl 4-(maleimidomethyl)cyclohexanecarboxylate with a hapten having the structure:

-continued wherein R is isobutyl; X$_1$ and X$_3$ are H; and X$_2$ is H—S—CH$_2$—CH(NH$_2$)—C(O)—.

2. The polyclonal antibody of claim 1, wherein the polyclonal antibody binds Polymyxin B with an IC$_{50}$ of 0.931 ng/ml and binds Colistin with an IC$_{50}$ of 1.191 ng/ml.

3. A polyclonal antibody selected from the group consisting of RS2790, RS2801, and RS2830, wherein the polyclonal antibody is raised against an immunogen having the structure Structure I Structure II wherein Z is —CH$_2$—CH(NH$_2$)—C(O)—,
wherein the accm includes keyhole limpet haemocyanin activated with N-succinimidyl 4-(maleimidomethyl)cyclohexanecarboxylate,
wherein the polyclonal antibody has a relative % cross-reactivity to Polymyxin B and Colistin at different antibody concentrations and different tracer concentrations as follows:

| Tracer dilution | Antibody RS2790 | | | | Antibody RS2801 | | | | Antibody RS2830 | | | |
| | 0.1 mg/ml | | 0.75 mg/ml | | 0.1 mg/ml | | 0.75 mg/ml | | 0.1 mg/ml | | 0.75 mg/ml | |
| | Col | Poly | Col | Poly | Col | Poly | Col | Poly | Col | Poly | Col | Poly |
|---|---|---|---|---|---|---|---|---|---|---|---|---|
| 1/50K | 5 | 100 | 8 | 100 | | | | | | | | |
| 1/100K | 23 | 100 | 59 | 100 | | | | | | | | |
| 1/500K | | | | | 20 | 100 | 67 | 100 | 6 | 100 | 8 | 100 |
| 1/1000K | | | | | 15 | 100 | 62 | 100 | 5 | 100 | 9 | 100 | wherein the tracer is a conjugate of horseradish peroxidase activated with N-succinimidyl 4-(maleimidomethyl)cyclohexanecarboxylate with a hapten having the structure:

Structure II wherein R is isobutyl; X$_1$ and X$_3$ are H; and X$_2$ is H—S—CH$_2$—CH(NH$_2$)—C(O)—.

4. A method for detecting or determining polymyxins in a sample, the method comprising the steps of contacting the sample with the polyclonal antibody of claim 1, and detecting or determining any polymyxins in the sample bound to the polyclonal antibody.

5. The method of claim 4, wherein the polymyxin is Polymyxin B and/or Colistin.

6. The method of claim 4, wherein the polymyxin is Polymyxin B.

7. The method of claim 4, wherein the polymyxin is Colistin.

8. The method of claim 4, wherein the polymyxin is Polymyxin B and Colistin.

9. A method of making an antibody comprising:
administering to a host animal an immunogen having the structure Structure I wherein Z is —CH$_2$—CH(NH$_2$)—C(O)—,
wherein the accm includes keyhole limpet haemocyanin activated with N-succinimidyl 4-(maleimidomethyl)cyclohexanecarboxylate; and
purifying the resulting antibody.

10. The method of claim 9, wherein the antibody is a polyclonal antibody.

\* \* \* \* \*